United States Patent
Aggarwal

[19]

[11] Patent Number: 6,063,920

[45] Date of Patent: May 16, 2000

[54] DINAPHTAZEPINIUM SALTS USEFUL AS ENANTIOSELECTIVE EPOXIDATION CATALYSTS

[75] Inventor: Varinder Kumar Aggarwal, Sheffield, United Kingdom

[73] Assignee: University of Sheffield, Western Bank, Sheffield, United Kingdom

[21] Appl. No.: 09/011,010

[22] PCT Filed: Aug. 7, 1996

[86] PCT No.: PCT/EP96/03551

§ 371 Date: Jun. 1, 1998

§ 102(e) Date: Jun. 1, 1998

[87] PCT Pub. No.: WO97/06147

PCT Pub. Date: Feb. 20, 1997

[30] Foreign Application Priority Data

Aug. 9, 1995 [GB] United Kingdom .................. 9516309

[51] Int. Cl.[7] ............................................... C07D 223/14
[52] U.S. Cl. ........................................................... 540/576
[58] Field of Search ............................................... 540/576

[56] References Cited

U.S. PATENT DOCUMENTS 5,360,568 11/1994 Madison et al. .......................... 252/102

OTHER PUBLICATIONS

Bohe et al., The Stereospecific Synthesis of a New Chiral Oxaziridinium Salt, Tetrahedron Letters, vol. 34, No. 45, pp. 7271–7274, 1993.

Mazaleyrat, Methode Simple De Synthese D'Agents De Transfert Chiraux Par Action D'un Agent Alkylant a Squelette Binaphtyle–1,1', Tetrahedron Letters, vol. 24, No. 12, pp. 1243–1246, 1993.

Aggarwal et al., Catalytic Asymmetric Synthesis of Epoxides Mediated by Chiral Iminium Salts, Chemical Communications, No. 2, pp. 191–192, Jan. 1996.

*Primary Examiner*—Mukund J. Shah
*Assistant Examiner*—Brenda Coleman
*Attorney, Agent, or Firm*—James M. Kanagy; Charles M. Kinzig

[57] ABSTRACT

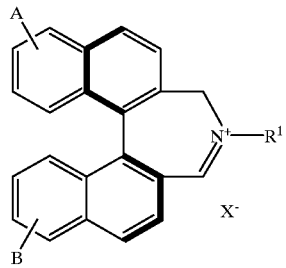

(Ia)

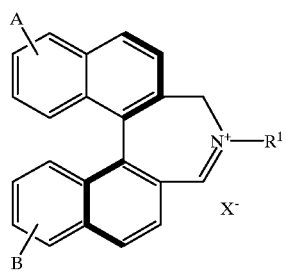

(Ib)

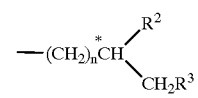

(a)

A compound of formula (Ia) of (Ib), wherein A and B each independently represents hydrogen or one, two or three naphthylidene substituents, which substituents are selected from $C_{1-6}$ alkyl, $C_{1-6}$ alkoxy, aryl, aryloxy, silyl and silyloxy; $R^1$ represents phenyl, $C_{1-6}$ alkyl, phenyl $C_{1-6}$ alkyl or a moiety of formula (a): wherein $R^2$ represents $C_{1-6}$ alkyl, phenyl or benzyl, $R^3$ represents H or $OR^4$ wherein $R^4$ is $C_{1-6}$ alkyl or $C_{1-6}$ alkylsilyl and n is zero or an integer 1 or 2; and $X^-$ is a counter ion; a process for the preparation of such compounds and the use of such compounds for enantioselectively epoxidising a prochiral olefin.

9 Claims, No Drawings

DINAPHTAZEPINIUM SALTS USEFUL AS ENANTIOSELECTIVE EPOXIDATION CATALYSTS

This application is a national stage entry under 35 U.S.C. § 371 of PCT/EP96/03551, filed Aug. 7, 1996.

This invention relates to novel compounds and the use of such compounds as catalysts in oxygen transfer reactions.

The catalytic asymmetric epoxidation of alkenes using chiral catalysts, in particular the salen manganese complexes of Jacobsen et al (International Patent Application, Publication Number WO/91/14694), is now well established methodology in asymmetric synthesis. The importance of these catalytic systems stems in the main from the versatility of application of the asymmetric epoxidation reaction itself. This versatility is due to the many and varied nucleophiles which can be used to open the substrate epoxide providing a concomitantly varied range of enantiomerically enriched products which are increasingly required for use for the manufacture of biologically important compounds such as pesticides, herbicides and pharmaceuticals.

In addition to organo-transition metal based catalysts, such as the Jacobsen catalysts purely organic asymmetric catalysts are also known. Thus Hanquet et al (Tetrahedron Letters, Vol. 34, no.45, pp7271–7274) have demonstrated that the oxaziridinium salt (1S, 2R, 3R, 4S)-N-methyl-1,2-oxido-3-methyl-4-phenyl-1,2,3,4-tetrahyroisoquinolinium tetrafluoroborate catalyses the asymmetric epoxidation of trans-stilbene and the asymmetric oxidation of methyl p-tolyl sulphide to the corresponding sulphoxide. The oxaziridinium salts are prepared in situ from a catalytic amount of an iminium salt and oxone (Hanquet et al C.R.Acad Sci., Paris, 1991, 313,SII, pp625–628).

Unlike the salen manganese complexes and other organo-transition metal based catalysts, the oxaziridinium catalysts do not function by means of radical intermediates. They may therefore be used with a wider range of alkene substrates as there is no requirement for π-stabilising groups on the alkene (to stabilise incipient radicals). Also, the oxidation reactions of the oxaziridinium catalysts are stereospecific in the sense that cis alkenes give cis epoxides and trans alkenes give trans epoxides. To data however, despite these advantages, the oxaziridinium catalysts have not provided oxidation systems for use on an industrial scale.

It has now been discovered that a novel series of oxaziridium salts show much promise in the catalytic asymmetric epoxidation of alkenes. The catalytic reaction employed is simple and robust enabling the use of readily available and cheap reagents as well as environmentally safe solvents.

Accordingly, in a first aspect, the invention provides a compound of formula (Ia) or (Ib):

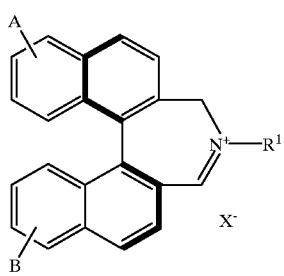

(Ia)

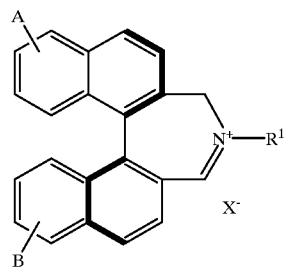

(Ib)

wherein A and B each independently represents hydrogen or one, two or three naphthylidene substituents, which substituents are selected from $C_{1-6}$ alkyl, $C_{1-6}$ alkoxy, aryl, aryloxy, silyl and silyloxy;

$R^1$ represents phenyl, $C_{1-6}$ alkyl, phenyl $C_{1-6}$ alkyl or a moiety of formula (a):

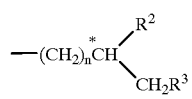

wherein $R^2$ represents $C_{1-6}$ alkyl, phenyl or benzyl, $R^3$ represents H or $OR^4$ wherein $R^4$ is $C_{1-6}$ alkyl or $C_{1-6}$ alkylsilyl and n is zero or an integer 1 or 2; and X is a counter ion.

Suitably, A represents hydrogen.

Suitably, B represents hydrogen.

Examples of $R^1$ when it represents $C_{1-6}$ alkyl are methyl and ethyl groups.

An example of $R_1$ benzyl.

Suitably, $R^2$ represents $C_{1-6}$ alkyl.

Suitably, $R^3$ represents $C_{1-6}$ alkyl.

Preferably, $R^1$ represents $C_{1-6}$ alkyl,

Values for the counter ion $X^-$ include $BF_4^-$, $Cl^-$, $Br^-$, $I^-$, $ClO_4^-$ and $PF_6^-$.

A preferred value for the counter ion $X^-$ is $BF_4^-$.

A suitable aryl group is a phenyl group.

As used herein, alkyl groups, whether presents alone or as part of other groups such as alkoxy or aralkyl groups, are alkyl groups having straight or branched carbon chains, containing 1 or 6 carbon atoms, e.g. methyl, ethyl, n-propyl, iso-propyl, n-butyl, isobutyl or tert-butyl groups.

The compounds of formula (Ia) or (Ib) may be prepared by reacting, as appropriate, a compound of formula (IIa) or (IIb):

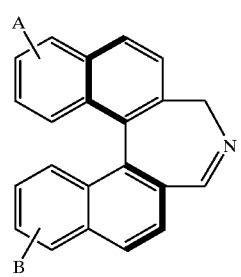

(IIa)

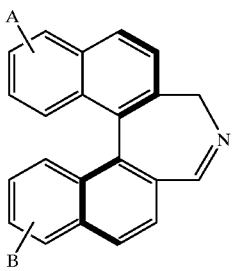

(IIb)

wherein A and B are as defined in relation to formula (I), with an alkylating agent of formula (III):

$$R^1-L^1 \quad (III)$$

wherein $R^1$ is as defined in relation to formula (I) and $L^1$ is a leaving group or atom; and thereafter salting the compound produced with a source of counter ion $X^-$.

$L^1$ usually represents halide, such as bromide or iodide, tosyl, or mesyl.

The reaction between the compounds of formulae (II) and (III) may be carried out with or without a solvent; when using a solvent it is suitably an organic solvent, generally an inert organic solvent such as methylene dichloride, at a low to elevated temperature such as a temperature in the range of from 0 to 100° C., conveniently at ambient temperature; preferably the reaction is carried out under anhydrous conditions; preferably the reaction is carried out in an inert atmosphere, for example under nitrogen.

The salting reaction with the source of counter ion $X^-$ may be carried out using any conventional procedure but is usually effected in the solvent used in the reaction, at ambient temperature.

The source of counter ion $X^-$ may be any conventional source such as an appropriate metal salt and especially a silver salt, conveniently however alkylating agent (III) is also the source of counter ion $X^-$; for example when preparing compounds of formula (Ia) or (Ib) wherein $R^1$ is $C_{1-6}$ alkyl and $X^-$ is $BF_4^-$, the compound of formula (II) is a compond $(R^{1a})_3OBF_4$, wherein $R^{1a}$ is $C_{1-6}$ alkyl, especially methyl.

The compounds of formula (IIa) and (IIb) may be prepared by oxidation of a chiral amine of formula (IV):

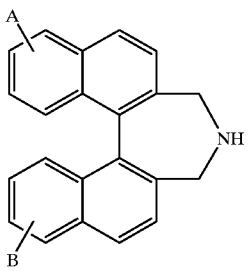

(IV)

wherein A and B are as defined in relation to formula (I), suitably using potassium permanganate as oxidant in the method of Fleischhacker et al, monatsh chem. 1989 120 765.

The chiral compounds of formula (IV) may be prepared from the racemic compound of formula (IV) using conventional resolution methods, for example, the method disclosed by Hawkins and Fu in Journal of Organic Chemistry 1986, 51, 2820–2822.

The compounds of formula (III) are known compounds or they may be prepared using methods analogous to those used to prepare known compounds, for example the methods disclosed by W. S. Johnson et al, Journal of American Chemical Society, 1963, 85, 1409.

The compounds of formula (IV) are known compound or they are prepared using methods analogous to those used to prepare known compounds, for example the methods disclosed by Hawkins and Fu ibidem.

The compounds of formula (Ia) and (Ib) wherein $R^1$ represents a moiety of the above defined formula (a), may be prepared, as appropriate, by cyclising a compound of formula (Va) or (Vb):

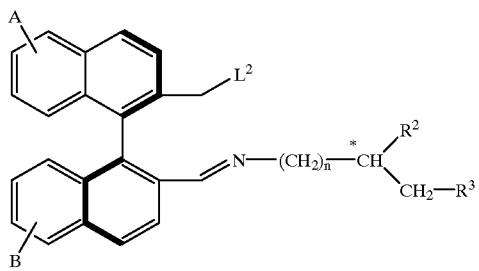

(Va)

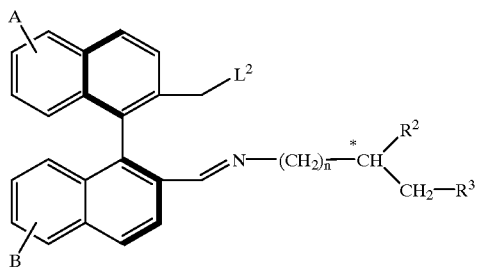

(Vb)

wherein A, B, $R^2$, $R^3$ and n are as defined in relation to formula (I) and $L^2$ represents a leaving group; and thereafter salting the compound produced with a source of counter ion $X^-$.

The cyclisation reaction of the compounds of formula (Va) and (Vb) may be carried out in an suitable organic solvent, usually an aprotic solvent such as acetone, at ambient or an elevated temperature, conveniently at the reflux temperature of the solvent.

The salting reaction with the source of counter ion $X^-$ may be carried out using any conventional procedure but is usually effected in the solvent used in the cyclisation reaction, at ambient temperature. The source of counter ion $X^-$ may be any conventional source such as an appropriate metal salt, for example when $X^-$ is $BF_4^-$ a suitable source is an alkali metal borotetrafluoride, such as sodium tetrafluoroborate or silver tetrafluoroborate.

The compounds of formula (Va) and (Vb) may be prepared by reacting, as appropriate, a compound of formula (VIa) or (VIb):

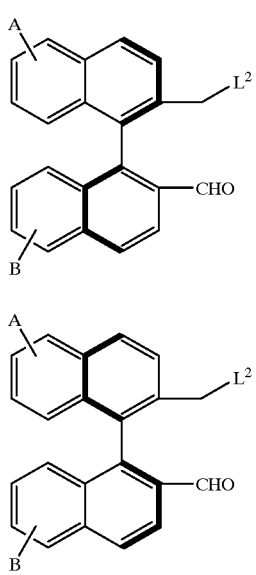

wherein A, B and L² are as defined in relation to formula (Va), with a compound of formula (VII):

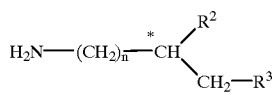

wherein R², R³ and n are as defined in relation to formula (I).

The reaction between the compound of formula (VIa) or (VIb) and the compound of formula (VII) may be carried out using any suitable organic solvent, generally an aprotic solvent such as tetrahydrofuran, usually at a low or medium elevated temperature such as a temperature in the range of from −78 to 50° C.

The compounds of formula (VII) are known compound or they may be prepared using methods analogous to those used to prepare known compounds, for example the methods disclosed by Evans et al, Organic Synthesis, Vol. 68, 1989, 77.

The compounds of formula (VIa) or (VIb) may be prepared in accordance with methods illustrated below:

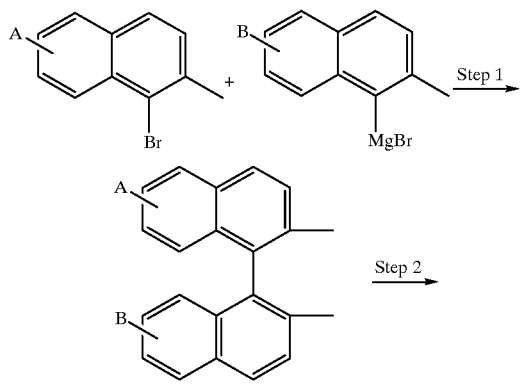

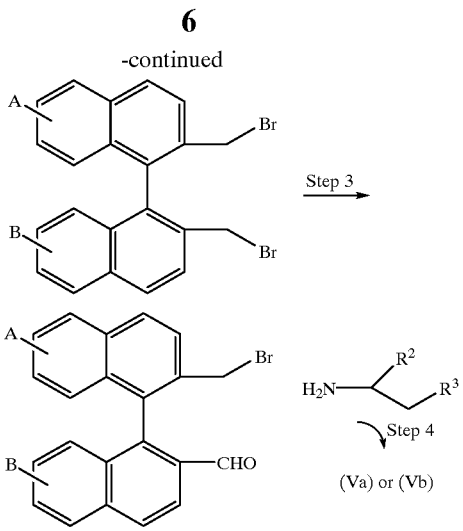

wherein A and B are as defined in relation to formula (I), the conditions of reaction and reagents used in for Steps 1 to 4 being those found in the following references:

Steps 1 and 2: N. Naigrot, J. P. Mazaleyrat, Synthesis, 1985, p 317.

Step 3: H. B. Hass, M. L. Bender, Org, Syn.,Coll. Vol. 4, 1963, 932.

Step 4: B. Bezas, L. Zervas, JACS, 1961, 83, 719.

As stated above the compounds of formula (I) are useful catalysts in the asymmetric epoxidation of alkenes. Accordingly, in a further aspect the invention provides a process for enantioselectively epoxidising a prochiral olefin such as 1-phenylcyclohexene, 1-methylcyclohexene, trans-stilbene and methylstilbene, which process comprises reacting the prochiral olefin with a nucleophilic oxidising agent in the presence of a catalyst, characterised in that the catalyst is a compound of formula (Ia) or (Ib):

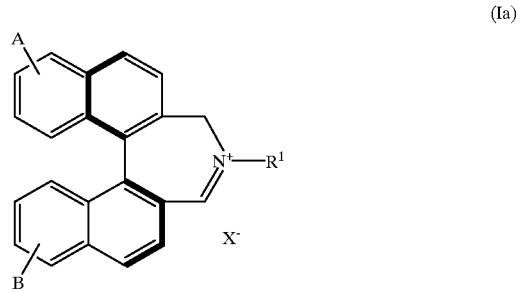

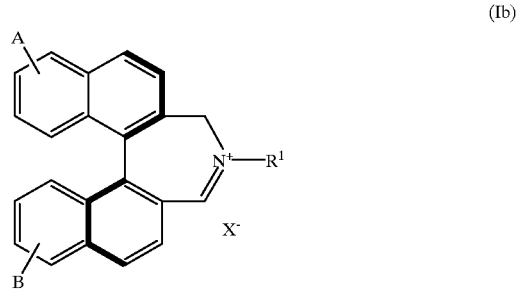

wherein A and B each independently represents hydrogen or one, two or three naphthylidene substituents, which substituents are selected from $C_{1-6}$ alkyl, $C_{1-6}$ alkoxy, aryl, aryloxy, silyl and silyloxy;

$R^1$ represents phenyl, $C_{1-6}$ alkyl, phenyl $C_{1-6}$ alkyl or a moiety of formula (a):

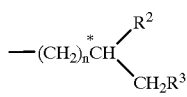

wherein R² represents $C_{1-6}$ alkyl, phenyl or benzyl;
R³ represents H or OR⁴ wherein R⁴ is $C_{1-6}$ alkyl or $C_{1-6}$ alkylsilyl and n is zero or an integer 1 or 2; and
X is a counter ion.

One suitable nucleophilic oxidising agent is provided by a mixture of oxone ($KHSO_5$) and $NaHCO_3$.

The epoxidation reaction may be carried out using any suitable procedure wherein the prochiral olefin, the nucleophilic oxidising agent and the compound of formula (Ia) or (Ib) are allowed to react thereby providing the required epoxide.

The reaction is carried out in an organic solvent such as acetonitrile, dimethysulphoxide, dimethylformamide or pyridine or in an organic solvent/water mixture such as aqueous acetonitrile.

Aqueous acetonitrile is a particularly apt reaction solvent when oxone/$NaHCO_3$ is the nucleophilic oxidising agent.

The reaction is carried out at a low to medium-elevated temperature such as a temperature in the range of from −20 to 50° C., preferably at ambient temperature.

Suitably, the reaction is carried out at a neutral or alkaline pH such as in the range of from pH 7 to 14, preferably it is carried out in the range of from pH 8 to 10.

Suitably the molar ratio of the compound of formula (Ia) or (Ib) to the prochiral olefin is in the range of from 1 to 20 mol %, preferably in the range of from 5 to 10 mol %.

The following preparation and examples illustrate the present invention.

IMINIUM SALT CATALYSTS
General Preparation Procedure

To a solution of the required imine in $CH_2Cl_2$ was added the corresponding alkylating agent. The reaction was left to react at room temperature until completion. The solvent was then removed and the residue was precipitated out in ether to give the desired salt.

EXAMPLE 1: (S-(+)-5,5-Dihydro-2H-dinaphth[2,1-c:1',2'-e]-N-methyl Azepine Tetrafluoroborate To a solution of (S)-imine from Preparation 1 (400 mg, 1.36 mmol) in dry $CH_2Cl_2$ (10 ml) was added under $N_2$, $Me_3OBF_4$ (222 mg, 1.5 mmol) in one portion. The reaction was left to react at room temperature under $N_2$ for 24 h. The solvent was removed and the residue was precipitated out in ether to give the desired salt (518 mg, 96%), $[\alpha]_D^{20}$+1070 (c 1.1 in $CH_2Cl_2$); $\delta_H$ (250 MHz; $CDCl_3$) 4.05 (3H, s, $CH_3$), 4.6 (1 H, d, J 12.5 Hz, ArCH'H), 4.95 (1 H, d, J 12.5Hz, ArCHH'), 7.0–8.25 (12 H, m, Ar—H), and 9.2 (1 H, s, CH=N); $\delta_C$ (62 MHz; $CDCl_3$) 48.76, 58.8, 125.29, 126.14, 126.78, 126.9, 127.12, 127.21, 127.5, 128.68, 129.54, 129.67, 130.12, 130.89, 131.41, 131.78, 131.93, 133.87, 135.29, 141.12, and 168.36; m/z (FAB) 308 (M⁺−87, 100%) (Found 308.1448. $C_{23}H_{18}N$ requires 308.1439).

EXAMPLE 2: (S)-(+)-5,5-Dihydro-2H-dinaphth[2,1-c:1',2'-e]-N-methyl Azepine Iodide A solution of (S)-imine from Preparation 1 (50 mg, 0.17 mmol) in iodomethane (2 ml) was stirred at room temperature, and very soon a yellow solid was formed in the reaction mixture. TLC of the reaction after 24 h showed only a small amount of starting material left. The remaining imine and excess of iodomethane were removed trituration with ether. After drying under high vacuum the desired compound was obtained as a yellow solid (72 mg, 97%); $\delta_H$ (250 MHz; $CDCl_3$) 4.25 (3 H, s, $CH_3$), 4.70 (1 H, d, J 13.1 Hz, ArCH'H), 4.85 (1 H, d, J 13.1 Hz, ArCHH'), 7.00–8.50 (12 H, m, Ar—H), and 10.50 (1 H, s, N=CH).

EXAMPLE 3: (S)-(+)-5,5-Dihydro-2H-dinaphth[2,1-c:1',2'-e]-N-methyl Azepine Perchlorate A solution of $AgClO_4$ (34.3 mg, 0.17 mmol) in acetone (1 ml) was added to a solution of (S)-iminium salt from Example 2 (72 mg, 0.16 mmol) in $CH_2Cl_2$ (1 ml). The solid formed was filtered off and the filtrate was concentrated to give the desired iminium salt which was precipitated from ether. After drying under high vacuum the desired compound was obtained as a yellow solid (60 mg, 90%), $[\alpha]_D^{20}$+769 (c 1.09 in acetone); $\delta_H$ (250 MHz; $CDCl_3$) 4.15 (3 H, s, $CH_3$), 4.70 (1 H, d, J 13 Hz, ArCH'H), 4.80 (1 H, d, J 13 Hz, ArCHH'), 7.0–8.2 (12 H, m, Ar—H), and 9.35 (1 H, s, N=CH); $\delta_C$ (100 MHz; $d_6$-acetone) 49.44, 59.19, 126.59, 126.64, 127.62, 127.85, 127.93, 128.03, 128.46, 129.58, 129.60, 130.01, 130.24, 130.26, 130.91, 131.76, 132.18, 132.40, 132.82, 134.83, 136.92, 141.86, and 169.98.

EXAMPLE 4: (R)-(−)-5,5-Dihydro-2H-dinaphth[2,1-c:1',2'-e]-N-methyl Azepine Hexfluorophosphate A solution of $AgPF_6$ (40.7 mg, 0.16 mmol) in acetone (1 ml) was added to a solution of (R)-iminium salt from Example 2 (70 mg, 0.16 mmol) in $CH_2Cl_2$ (2 ml). The solid formed was filtered off and the filtrate was concentrated to give the desired iminium salt which was precipitated from ether. After drying under high vacuum the desired compound was obtained as a yellow solid (65 mg, 92%), $[\alpha]_D^{20}$−769 (c 1.25 in acetone); $\delta_H$ (250 MHz; $CDCl_3$) 4.09 (3 H, s, $CH_3$), 4.64 (1 H, d, J 13 Hz, ArCH'H), 4.89 (1 H, d, J 13 Hz, ArCHH'), 7.00–8.25 (12 H, m, Ar—H), and 9.12 (1 H, s, N=CH); $\delta_C$ (100 MHz; $CD_2Cl_2$) 49.22, 59.60, 125.17, 125.95, 126.67, 127.42, 127.52, 127.82, 128.18, 129.02, 129.07, 129.96, 130.24,, 130.97, 131.42, 131.94, 32.37, 132.44, 134.37, 135.02, 135.92, 142.19, and 168.56.

EXAMPLE 5: (S)-(+)-5,5-Dihydro-2H-dinaphth[2,1-c:1',2'-e]-N-ethyl Azepine Iodide A solution of (S)-imine from Preparation 1 (50 mg, 0.17 mmol) in iodoethane (2 ml) was stirred at room temperature, and yellow solid was soon formed in the reaction mixture. TLC of the reaction after 24 h showed that only a small amount of starting material was left. The remaining imine and excess iodoethane were removed by trituration with ether. After drying under high vacuum the desired product was obtained as a yellow solid (60 mg, 98%), m.p.>200° C. (dec.), $[\alpha]_D^{20}$+878 (c 0.41 in $CH_2Cl_2$); $\delta_H$ (250 MHz; $CDCl_3$) 1.51 (3 H, t, J 7 Hz, $CH_3$), 4.45–4.75 (2 H, m, $CH_2CH_3$), 4.6 (1 H, d, J, 12.5 Hz, ArCH'H), 4.95 (1 H, d, J 12.5 Hz, ArCHH'), 7.00–8.60 (12 H, m, Ar—H), and 10.60 (1 H, s, N=CH); $\delta_C$ (100 MHz; $CD_2Cl_2$) 14.30, 57.75, 57.86, 125.21, 127.09, 127.42, 127.62, 127.68, 127.89, 128.93, 129.04, 129.75, 129.84, 130.62, 131.72, 131.93, 132.04, 132.45, 134.23, 135.41, 135.80, 141.95, and 168.23; m/z (FAB) 323 (M⁺−128), 322 (M⁺−129, 100%), and 308 (M⁺−141); HRMS: m/z calc. 322.1604. $C_{24}H_{20}N$ (M⁺−127) found 322.1596.

EXAMPLE 6: (R)-(−)-5,5-Dihydro-2H-dinaphth[2,1-c:1',2'-e]-N-ethyl Azepine Tetrafluoroborate A solution of $AgBF_4$ (40 mg, 0.2 mmol) in acetone (1 ml) was added to a solution of the (R)-iminium salt from Example 5 (76 mg, 0.17 mmol) in $CH_2Cl_2$ (2 ml). The solid (AgI) formed was removed by filtration. The resulting foam, obtained by concentration of the filtrate, was triturated with ether to gave the desired product as a yellow gum (59 mg, 84%); $[\alpha]_D^{20}$−832 (c 0.87 in acetone); $\delta_H$ (250 MHz; $CD_2Cl_2$) 1.50 (3 H, t, J 6.5 Hz, $CH_3$), 4.25 (2 H, q, J 6.5 Hz, CH₂CH₃), 4.53 (1 H, d, J 13 Hz, ArCH'H), 4.94 (1 H, d, J 13 Hz, ArCHH'), 6.9–8.15 (12 H, m, Ar—H), and 9.13 (1 H, s, N=CH); $\delta_C$ (100 MHz; CD₂Cl₂) 13.87, 57.49, 58.38, 125.46, 126.33, 126.88, 127.02, 127.10, 127.15, 127.86, 128.86, 128.97, 129.67, 129.97, 130.64, 131.60, 131.87, 132.01, 132.40, 134.25, 135.82, 141.86, and 167.90.

EXAMPLE 7: (S)-(+)-5,5-Dihydro-2H-dinaphth[2,1-c:1',2'-e]-N-benzyl Azepine Bromide A solution of (S)-imine from Preparation 1 (50 mg, 0.17 mmol) in benzyl bromide (2 ml) was left to stir at room temperature for 2 days. TLC of the reaction showed a small amount of starting material left. Excess benzyl bromide was removed under vacuum and the residue was triturated with ether to removed the unreacted starting material and trace amounts of benzyl bromide. After drying under high vacuum the desired compound was obtained as a yellow solid (75 mg, 95%), m.p. 150–152° C. (dec.), $[\alpha]_D^{20}$+450 (c 1.48 in CH₂Cl₂); $\delta_H$ (250 MHz; CDCl₃) 4.45 (1 H, d, J 13.4 Hz, ArCH'H), 4.90 (1 H, d, J 13.4 Hz, ArCHH'), 5.80 (1 H, d, J 13.0 Hz, PhCH'H), 5.94 (1 H, d, J 13.0 Hz, PhCHH'), 6.75–8.6 (17 H, m, Ar—H), and 11.22 (1 H, s, N=CH); $\delta_C$ (100 MHz; CDCl₃) 56.55, 65.28, 124.68, 126.86, 126.94, 127.19, 127.44, 128.47, 128.65, 128.74, 128.97, 129.35, 129.49, 129.87, 130.19, 130.90, 131.03, 131.45, 131.60, 133.44, 135.34, 141.42, and 169.45; m/z (FAB) 385 (M⁺−79), 384 (M⁺−80, 100%); HRMS: m/z calc. 384.1745 C₂₉H₂₂N (M⁺−80) requires 384.1752.

EXAMPLE 8: (R)-(−)-5,5-Dihydro-2H-dinaphth[2,1-c:1',2'-e]-N-benzyl Azepine Tetrafluoroborate To a solution of (R)-bromide salt from Example 7 (prepared from 50 mg, 0.17 mmol of (R)-imine from Preparation 1) in CH₂Cl₂ (2 ml) was added AgBF₄ (40 mg, 0.2 mmol). The solid (AgBr) formed was separated and the filtrate concentrated. The resulting foam was triturated with ether to gave the desired product as a yellow gum (48 mg, 60%); $[\alpha]_D^{20}$−637 (c 0.6 in acetone); $\delta_H$(250 MHz; CDCl₃) 4.55 (1 H, d, J 12.5 Hz, ArCH'H), 4.55 (1 H, d, J 12.5 Hz, ArCH'H), 4.95 (1 H, d, J 12.5 Hz, ArCHH'), 5.48 (1 H, d, J 14 Hz, PhCH'H), 5.58 (1 H, d, J 13 Hz, PhCHH'), 6.65–8.16 17 H, m, Ar—H), and 9.55 (1 H, s, N=CH); $\delta_C$ (100 MHz; CDCl₃) 56.54, 66.12, 124.71, 126.60, 126.63, 126.92, 127.14, 127.51, 128.50, 128.66, 129.43, 129.47, 129.70, 130.01, 130.18, 130.29, 130.64, 130.95, 131.05, 131.45, 131.60, 133.46, 135.41, 135.44, 141.56, and 168.17.

CATALYTIC EPOXIDATION USING IMINIUM SALT CATALYSTS

General Procedure

To a solution of alkene (0.5 mmol) in a mixture of acetonitrile (4.5 ml) and water (1–2 drops) were added first finely crushed NaHCO₃ (2 mmol) and oxone (0.5 mmol) then the catalyst (0.05 mmol or 0.025 mmol). The resulting yellow suspension was allowed to react at room temperature, under good stirring. The reaction was monitored using thin layer chromatography (TLC). Usually towards the end of the reaction the colour of the mixture changed from bright yellow to nearly colourless. Water was added to the reaction mixture followed by extraction into methylene dichloride. The organic extracts were combined and dried over anhydrous sodium sulphate. Concentration on a rotary evaporator gave a material which was purified (column chromatography) to give the desired epoxide.

EXAMPLE 1: Preparation of Phenyl Cyclohexene Oxide

To a solution of phenyl cyclohexene (79 mg, 0.5 mmol) in a mixture of acetonitrile (4.5 ml) and water (2 drops) were added first finely crushed NaHCO₃ (168 mg, 2 mmol) and oxone (307 mg, 0.5 mmol) then the catalyst (0.05 mmol). The resulting yellow suspension was allowed to react at RT, under good stirring. TLC was used to follow the reaction which indicated that the reaction was finished in 2 h. Water (3 ml) was added to the reaction mixture followed by extraction into methylene dichloride. The organic extracts were combined and dried over anhydrous sodium sulphate. Concentration on a rotary evaporator gave a material which was purified on a column using 2% ethyl acetate:petrol mixture as eluent to give the desired compound as a colourless oil. (72 mg, 83% yield, 70% e.e).

The epoxidation of phenyl cyclohexene to phenyl cyclohexene oxide was then carried out using other catalysts of the invention. The results obtained are shown in Table 1.

TABLE 1

| Example No. | R¹ | X | Yield % | ee % |
|---|---|---|---|---|
| 1 | Me | BF₄ | 83 | 70 |
| 3 | Me | ClO₄ | 54 | 74 |
| 4 | Me | PF₆ | 48 | 61 |
| 5 | Et | I | 55 | 78 |
| 6 | Et | BF₄ | 78 | 76 |
| 7 | Bn | Br | 71 | 74 |
| 8 | Bn | BF₄ | 78 | 73 |

Preparation 1: (R(−) and S(+) 5,5-Dihydro-2H-dinaphth[2,1-c:1',2'-e]Azepine

To a solution of (R)- or (S)-amine (295 mg, 1 mmol) (Journal of Organic Chemistry, 1986, 51, 2820–2822) in THF (5 ml) was added KMnO₄ (648 mg, 4 mmol). The reaction was allowed to react at room temperature for 5 h before the solid was removed by filtration. Concentration of the filtrate followed by purification on column using ethyl acetate:petrol (1:1) as eluant gave the desired compound as a syrup (234 mg, 80%), (S)-isomer, $[\alpha]_D^{20}$+1363.7, (c 1.19 in CH₂Cl₂); (R)-isomer, $[\alpha]_D^{20}$−1363.7, (c 1.19 in CH₂Cl₂); Both isomers: $\delta_H$ (250 MHz; CDCl₃) 3.95 (1 H, dd, J 2.2 Hz and 11 Hz, ArCH'H), 4.96 (1 H, d, J 11 Hz, ArCHH'), 7.0–8.1 (12 H, m, Ar—H), and 8.6 (1 H, d, J 2.2 Hz, CH=N); $\delta_C$ (62 MHz; CDCl₃) 55.90, 124.36, 125.27, 125.87, 126.05, 126.42, 126.69, 127.16, 127.49, 128.07, 128.25, 128.44, 129.18, 130.49, 131.70, 132.08, 132.34, 132.99, 135.04, 136.99, 140.96, and 162.47; m/z (FAB) 294 (M⁺+1, 100%), 154 (M⁺−139), and 136 (M⁺−157)(Found 294.1275.C₂₂H₁₆N requires 294.1283).

I claim:

1. A compound of formula (Ia) or (Ib):

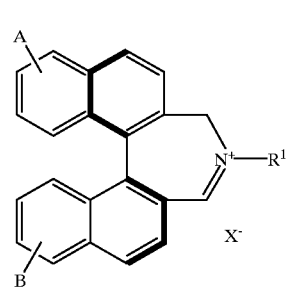

(Ia)

(Ib)

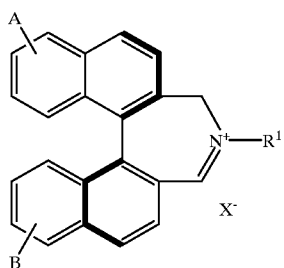

wherein A and B each independently represents hydrogen or one, two or three naphthylidene substituents, which substituents are selected from $C_{1-6}$ alkyl, $C_{1-6}$ alkoxy, aryl, aryloxy, silyl and silyloxy;

$R^1$ represents phenyl, $C_{1-6}$ alkyl, phenyl $C_{1-6}$ alkyl or a moiety of formula (a):

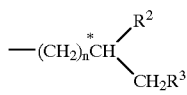

wherein $R^2$ represents $C_{1-6}$ alkyl, phenyl or benzyl, $R^3$ represents H or $OR^4$ wherein $R^4$ is $C_{1-6}$ alkyl or $C_{1-6}$ alkylsilyl and n is zero or an integer 1 or 2; and X⁻ is a counter ion.

2. A compound according to claim 1, wherein A represents hydrogen and B represents hydrogen.

3. A compound according to claim 1 wherein $R^1$ represents $C_{1-6}$ alkyl.

4. A compound according to claim 1, wherein $R^1$ represents methyl or ethyl.

5. A compound according to claim 1, wherein counter ion X⁻ is selected from the list consisting of: $BF_4^-$, Cl⁻, Br⁻, I⁻, $ClO_4^-$ and $PF_6^-$.

6. A compound according to claim 1, wherein counter ion X⁻ is $BF_4^-$.

7. A compound according to claim 1, selected from the list consisting of:
- (S)-(+)-5,5-dihydro-2H-dinaphth[2,1-c:1',2'-e]-N-methyl azepine tetrafluoroborate;
- (S)-(+)-5,5-dihydro-2H-dinaphth[2,1-c:1',2'-e]-N-methyl azepine iodide;
- (S)-(+)-5,5-dihydro-2H-dinaphth[2,1-c:1',2'-e]-N-methyl azepine perchlorate;
- (R)-(−)-5,5-dihydro-2H-dinaphth[2,1-c:1',2'-e]-N-methyl azepine hexfluorophosphate;
- (S)-(+)-5,5-dihydro-2H-dinaphth[2,1-c:1',2'-e]-N-ethyl azepine iodide;
- (R)-(−)-5,5-dihydro-2H-dinaphth[2,1-c:1',2'-e]-N-ethyl azepine tetrafluoroborate;
- (S)-(+)-5,5-dihydro-2H-dinaphth[2,1-c:1',2'-e]-N-benzyl azepine bromide; and
- (R)-(−)-5,5-dihydro-2H-dinaphth[2,1-c:1',2'-e]-N-benzyl azepine tetrafluoroborate.

8. A process for the preparation of the compounds of formula (Ia) and (Ib) which process comprises reacting, as appropriate, a compound of formula (IIa) or (IIb):

(IIa)

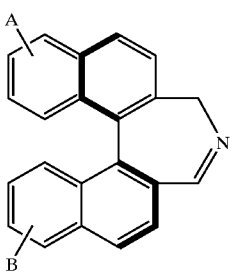

(IIb)

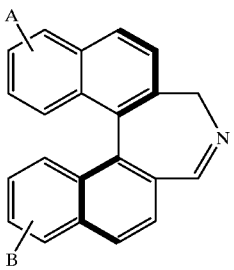

wherein A and B each independently represents hydrogen or one, two or three naphthylidene substituents, which substituents are selected from $C_{1-6}$ alkyl, $C_{1-6}$ alkoxy, aryl, aryloxy, silyl and silyloxy;

$R^1$ represents phenyl, $C_{1-6}$ alkyl, phenyl $C_{1-6}$ alkyl or a moiety of formula (a):

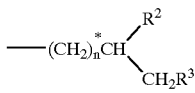

wherein $R^2$ represents $C_{1-6}$ alkyl, phenyl or benzyl, $R^3$ represents H or $OR^4$ wherein $R^4$ is $C_{1-6}$ alkyl or $C_{1-6}$ alkylsilyl and n is zero or an integer 1 or 2; with an alkylating agent of formula (III):

$$R^1\text{-}L^1 \qquad \text{(III)}$$

wherein $R^1$ is as defined in relation to formula (II) or (III) and $L^1$ is a leaving group or atom; and thereafter salting the compound produced with a source of counter ion X⁻.

9. A process for enantioselectively epoxidising a prochiral olefin which process comprises reacting the prochiral olefin with a nucleophilic oxidizing agent in the presence of a catalyst, characterized in that the catalyst is a compound of formula (Ia) or (Ib):

(Ia)

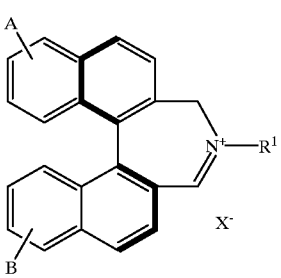

-continued (Ib)

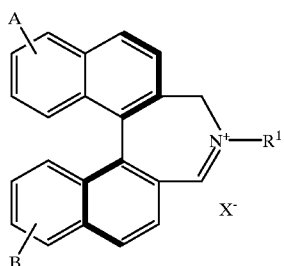

wherein A and B each independently represents hydrogen or one, two or three naphthylidene substituents, which substituents are selected from $C_{1-6}$ alkyl, $C_{1-6}$ alkoxy, aryl, aryloxy, silyl and silyloxy;

$R^1$ represents phenyl, $C_{1-6}$ alkyl, phenyl $C_{1-6}$ alkyl or a moiety of formula (a):

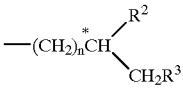

wherein $R^2$ represents $C_{1-6}$ alkyl, phenyl or benzyl;

$R^3$ represents H or $OR^4$ wherein $R^4$ is $C_{1-6}$ alkyl or $C_{1-6}$ alkylsilyl and n is zero or an integer 1 or 2; and $X^-$ is a counter ion.

* * * * *